United States Patent
Peterson et al.

(10) Patent No.: US 12,102,498 B2
(45) Date of Patent: Oct. 1, 2024

(54) DENTAL CURING LIGHT AND METHOD

(71) Applicant: Garrison Dental Solutions, L.L.C., Spring Lake, MI (US)

(72) Inventors: Steven H. Peterson, Martin, MI (US); Mark A. Cargill, Grand Rapids, MI (US)

(73) Assignee: Garrison Dental Solutions, LLC, Spring Lake, MI (US)

( * ) Notice: Subject to any disclaimer, the term of this patent is extended or adjusted under 35 U.S.C. 154(b) by 20 days.

(21) Appl. No.: 18/077,373

(22) Filed: Dec. 8, 2022

(65) Prior Publication Data
US 2023/0102501 A1     Mar. 30, 2023

Related U.S. Application Data

(62) Division of application No. 16/190,368, filed on Nov. 14, 2018, now Pat. No. 11,589,971.

(51) Int. Cl.
*A61B 1/24* (2006.01)
*A61B 1/00* (2006.01)
(Continued)

(52) U.S. Cl.
CPC ........ *A61C 19/004* (2013.01); *A61B 1/00045* (2013.01); *A61B 1/24* (2013.01);
(Continued)

(58) Field of Classification Search
CPC ....... A61C 19/004; A61C 19/003; A61C 5/00; G06T 7/55; G06T 7/20; G06T 7/50; A61B 1/00045; A61B 1/24; A61B 1/00043
(Continued)

(56) References Cited

U.S. PATENT DOCUMENTS 6,382,967 B1   5/2002   Rohner et al.
9,161,828 B2   10/2015  Senn et al.
(Continued)

FOREIGN PATENT DOCUMENTS

CN   2238025    10/1996
EP   3 173 062   5/2017
(Continued)

OTHER PUBLICATIONS

EP 3173062 A1 machine translation (Year: 2015).*
(Continued)

*Primary Examiner* — Ralph A Lewis
*Assistant Examiner* — Mirayda A Aponte
(74) *Attorney, Agent, or Firm* — Warner Norcross + Judd LLP

(57) ABSTRACT

The specification discloses a dental curing light including 1) a light engine, 2) a coaxially aligned, camera-based viewing system, and 3) a control system providing a variety of safety features and simplified, operator-friendly operation. The camera's field of view (FOV) is coaxial with the centerline of the curing beam of the light engine. The curing light includes a multi-planar dichroic mirror (MDM) providing viewing and light beam direction aligned with the target. The MDM provide multiple images to the camera from different angles. The camera provides real-time measurement of light intensity reflected back from the targeted surface. Using the multiple image portions reflected by the multi-planar dichroic mirror, the control system computes the distance between the curing light and the target. The reflected intensity and the calculated distance enable the control system to compute a light engine irradiance to achieve a desired irradiance at the targeted surface.

6 Claims, 6 Drawing Sheets

(51) Int. Cl.
*A61C 5/00* (2017.01)
*A61C 13/15* (2006.01)
*G06T 7/20* (2017.01)
*G06T 7/55* (2017.01)

(52) U.S. Cl.
CPC .................. *A61C 5/00* (2013.01); *G06T 7/20* (2013.01); *G06T 7/55* (2017.01)

(58) Field of Classification Search
USPC .......................................................... 433/29
See application file for complete search history.

(56) References Cited

U.S. PATENT DOCUMENTS

| | | | |
|---|---|---|---|
| 9,763,760 | B2 | 9/2017 | Senn et al. |
| 9,883,931 | B2 | 2/2018 | Gente et al. |
| 10,076,390 | B2 | 9/2018 | Senn |
| 10,182,891 | B2 | 1/2019 | Brotzge et al. |
| 10,231,810 | B2 | 3/2019 | Gramann et al. |
| 10,271,720 | B2 | 4/2019 | Fink et al. |
| 2006/0239005 | A1 | 10/2006 | De Godzinsky |
| 2007/0121786 | A1 | 5/2007 | Okawa et al. |
| 2009/0087050 | A1 | 4/2009 | Gandryra |
| 2013/0323673 | A1 | 12/2013 | Hakomori et al. |
| 2014/0242538 | A1 | 8/2014 | Senn |
| 2015/0202032 | A1 | 7/2015 | Benz |
| 2015/0250572 | A1* | 9/2015 | Gramann .............. A61C 19/004 433/29 |
| 2016/0287364 | A1 | 10/2016 | Pauler et al. |
| 2017/0172403 | A1 | 6/2017 | Fink et al. |
| 2017/0370642 | A1 | 12/2017 | Tommasini |
| 2018/0296310 | A1 | 10/2018 | Benz |
| 2018/0364464 | A1 | 12/2018 | Senn et al. |
| 2019/0374320 | A1 | 12/2019 | Schmid et al. |
| 2020/0030070 | A1 | 1/2020 | Gerlach et al. |
| 2020/0146797 | A1 | 5/2020 | Peterson et al. |

FOREIGN PATENT DOCUMENTS

| | | | | |
|---|---|---|---|---|
| EP | 3173062 A1 * | 5/2017 | ........... A61C 19/003 |
| WO | 2016/044549 | 3/2016 | |
| WO | 2017/093206 | 6/2017 | |
| WO | 2018/085351 | 5/2018 | |
| WO | 2018/098107 | 5/2018 | |
| WO | 2018/227077 | 12/2018 | |

OTHER PUBLICATIONS

U.S. Appl. No. 62/598,832, filed Dec. 14, 2017.
International Search Report and Written Opinion from PCT/US2019/054512 dated Jan. 29, 2020.

* cited by examiner

DENTAL CURING LIGHT AND METHOD

BACKGROUND OF THE INVENTION

The present invention relates to dental curing lights and to methods of using such lights to cure dental composites.

Dental curing lights and methods of using such lights to cure dental composites are well known and widely used. Exemplary lights and methods are disclosed in U.S. application Ser. No. 14/857,273 filed Sep. 17, 2015 entitled "Dental Curing Light"; U.S. application No. 62/517,530 filed Jun. 9, 2017 entitled "Curing Light Device Assembly"; U.S. application Ser. No. 15/797,801 filed Oct. 30, 2017 entitled "Dental Curing Light"; and U.S. application 62/598,832 filed Dec. 14, 2017 entitled "Curing Light with Integrated Feedback Sensor". The disclosures of these applications are incorporated by reference.

Dental curing lights are used to cross-polymerize (i.e. harden) the resins used in dental composite fillings. Dental curing lights have trended toward blue LED technology and relatively high-power lights to address issues of "under cure" and also to reduce the time required to achieve a "full cure" of the freshly placed composite filling. With increased power levels, curing times have been reduced from two or more minutes to just a few seconds.

However, the higher power lights have introduced several power-related concerns related to over-exposure, or more specifically, the rate of exposure. First, composite cures resulting from required energy being delivered too quickly (i.e. excessive levels of irradiance) have proven to be less reliable with a higher tendency to have issues such as shrinkage, varied degree of cure, and higher levels of internal stress. Second, the higher power levels have the potential to elevate the temperature of the treated tooth to undesirable levels that can cause irreversible damage to the vitality of the tooth pulp tissue. Third, the higher power levels can result in the unintended direct exposure of tongue, cheek, or gingival tissues to high irradiance levels (typically due to misalignment of the curing light) that in turn can cause painful and, in some cases, severe burns to those unintentionally irradiated tissues. The potential for tissue damage is exacerbated because red or pink tissues absorb a greater percentage of the blue light than does a white tooth, and therefore the red and pink tissues can heat up more quickly.

Handheld curing lights contribute to significant degrees of variability in total exposure during curing. A first variability factor is distance. Depending on the optical design of the curing light and its effective numerical aperture (NA), a variation in irradiance of 5 to 1 can easily be introduced with nothing more than the typical variation in the distance between the curing light and the tooth. A second variability factor is angle. Cosine effects can reduce irradiance 30% or more because of angular variations between the axis of the beam and the "normal" vector of the surface being exposed. A third variability factor is aim. The curing beam can be easily misdirected and pointed at the wrong area of the tooth, especially given the difficulty of the operator (e.g. dentist) being able to view the exact beam placement after the dental curing light is in position, because the curing light often blocks a clear view of the prepared area of the tooth.

The range and variety of composites for dental restoration have grown in part because of consumer expectations. One of those expectations, especially as use of composites on anterior teeth has grown, is that the composites be "shade matched" to have a similar shade to the natural tooth that they are being applied to. Consequently, a wide variety of composite shades are available. As the range of shade offerings expands, so to have the ranges of optical curing energy needed to safely complete the cure. Darker shades naturally result in more internal attenuation of the blue curing light as the light is scattered and transmitted through the freshly placed composite. This results in significantly increased energy requirements when curing darker shades.

SUMMARY OF THE INVENTION

The present invention provides a dental curing light including 1) a light engine, 2) a coaxially aligned, camera-based viewing system, and 3) a control system providing a variety of safety features and simplified, operator-friendly operation.

The camera's field of view (FOV) is coaxial with the centerline of the curing beam of the light engine. The camera includes a multi-planar dichroic mirror (MDM) providing viewing and light beam direction aligned with the intended target during the entire period of cure. The camera enables precise real-time measurement of light intensity reflected back from the targeted surface. Using the multiple image portions reflected by the multi-planar dichroic mirror, the control system computes the distance between the curing light and the target. The reflected intensity and the calculated distance enable the control system to compute a light engine irradiance to achieve a desired irradiance at the targeted surface. The control system uses the reflected irradiance as feedback to maintain the desired target irradiance value by "closing the loop" for driving the curing LEDs in real time for the duration of the light cure—independent of operator-induced height and angle variations in the positioning of the curing light relative to the tooth.

The present curing light enables the user to cure a composite restoration within the prepared area of a tooth simply and accurately. The curing light provides a reliable, consistent, known delivery of energy per unit area to a composite restoration, wherein the energy is independent of user-induced variations of distance and angle between the curing light and the targeted tooth. This assures that a reliable and complete cure is achieved with one cure rather than needing to re-cure multiple times, for example, just to make sure that there is no under cure. The curing light reduces the likelihood that the tooth pulp tissue and the adjacent gingival tissue will be over-heated due to 1) the use of multiple cures and/or 2) drifting off the target.

The present invention results in several advantages. First, the targeted composite accurately receives the desired amount of optical energy (e.g. joules per square centimeter) as established by its manufacturer to ensure a proper and complete cure. Second, the composite receives the desired energy over the recommended period of time. Third, the composite receives the desired energy in one cure, eliminating the need for second, third, or even additional cures. Fourth, the composite does not receive excessive energy and/or energy delivered over too short a period of time, thereby reducing the likelihood of overheating of localized tissue and tooth pulp. Fifth, the curing light more accurately remains on the intended target area.

These and other advantages and features of the invention will be more fully understood and appreciated by reference to the description of the current embodiment and the drawings.

DESCRIPTION OF THE CURRENT EMBODIMENTS

Figure 1:
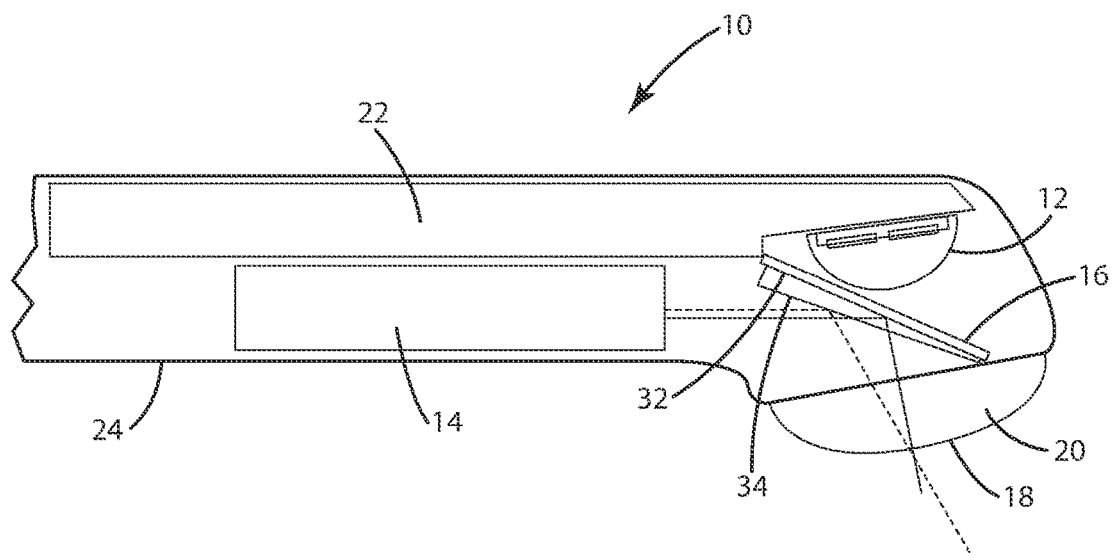
FIG. 1 is a cross-sectional view of the dental curing light of the present invention directed at a tooth.

Before the embodiments of the invention are explained, it is to be understood that the invention is not limited to the details of operation or to the details of construction; and the arrangement of the components set forth in the following description or illustrated in the drawings. The invention may be implemented in various other embodiments and may be practiced or carried out in alternative ways not expressly disclosed herein.

In addition, it is to be understood that the phraseology and terminology used herein are for the purpose of description and should not be regarded as limiting. The use of "including" and "comprising" and variations thereof encompasses the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one or more of X, Y or Z individually, and any combination of any one or more of X, Y and Z, for example, X, Y, Z; X, Y; X, Z; and Y, Z.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

I. Dental Curing Light

A dental curing camera constructed in accordance with a preferred embodiment of the invention is illustrated in FIG. 1 and generally designated 10. The curing light 10 includes a curing light engine 12, a camera 14, and a multi-planar dichroic mirror (MDM) 16.

The curing light engine 12 currently is LED-based, includes good optics, and provides relatively high optical power (i.e. greater than 2000 mW per cm$^2$). The light engine currently includes one or more LEDs. Alternatively, the curing light engine 12 may be any light engine now known or later developed. The output of the light engine 12, especially when LED-based, may be controlled relatively accurately. As currently constructed, the light engine includes an optical delivery system or lens 20 that is capable of sustaining, for example, at least 2000 mW per cm$^2$ at a target distance of 10 mm from the tip 18. Preferably, the profile of irradiance generated through the lens 20 across its beam is homogenous within 20% or so of the average power across the tip 18 (i.e. a beam shape that yields a high "top hat" factor).

The curing light includes a heat sink 22 to which the light engine 12 is operatively connected for heat dissipation. The heat sink 22 may be as simple as a copper rod. The heatsink may be any suitable device now known or later developed.

Although not specifically shown, the light engine 12 includes an LED power control as known to those skilled in the art. The power control (a) turns the LEDs on and off and (b) manages the level of output power in real time when the LEDs are on. Although not specifically shown, the power control is in turn controlled by a curing light control to control the output of the LEDs.

The camera 14 in the current embodiment is a relatively small cylindrical camera. The camera 14 is selected to fit within the handheld housing 24. The camera 14 preferably includes an integrated broadband illumination source. The camera may include an auto-focus function or capability as is or becomes known to those skilled in the art.

The mirror 16 enables coaxial alignment of the camera's field of view with the curing beam axis. The dichroic mirror is highly transmissive and partially reflective. The spatial and spectral properties of the mirror 16 provide excellent optical efficiency of the curing beam. The mirror 16 preferably is a dichroic mirror tuned to the blue curing wavelengths with efficiency, and is reflective over the remainder of the visual spectrum. Alternatively, the mirror may be a highly transmissive and partially reflective glass plate. The reflective surface or mirror is placed in the path of the curing beam at a 45° angle or other appropriate angle to enable the field of view of the camera 14 to be coaxially aligned with the centerline of the curing beam.

Figure 3:
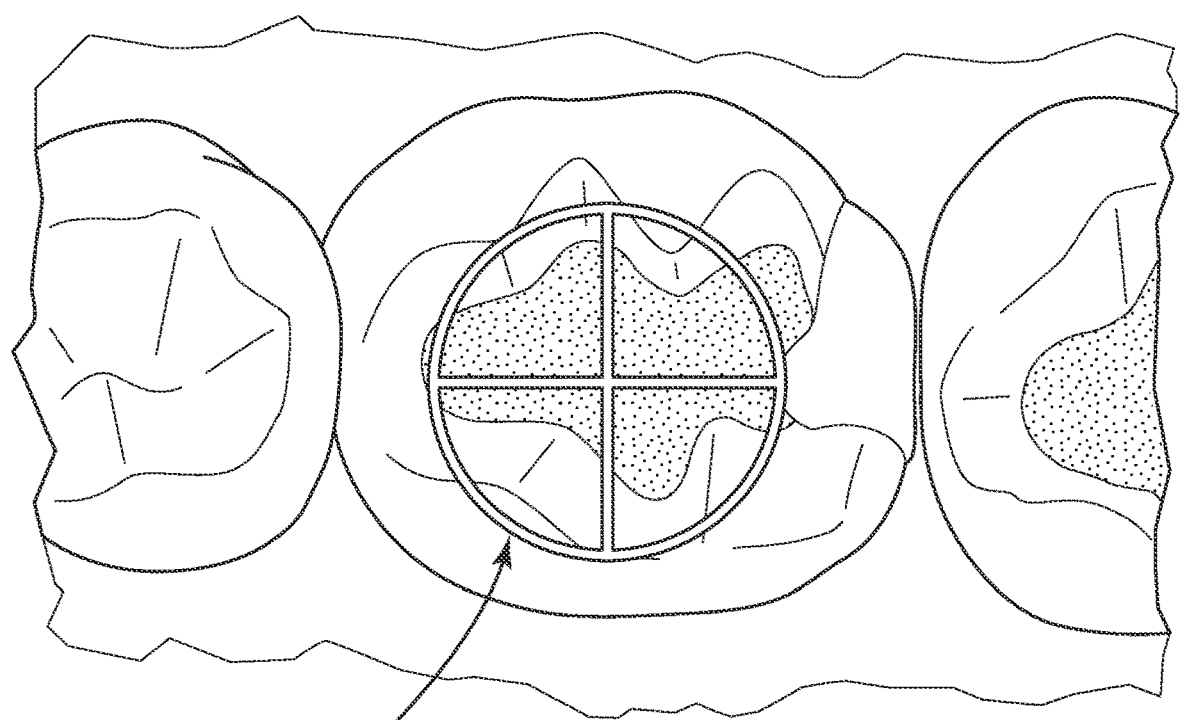
FIG. 3 is a display of the tooth image of FIG. 2 and additionally including a targeting graphic superimposed on the tooth image.

Although not shown, the curing light includes a GUI display. The GUI display may be part of the curing light 10. Alternatively, the GUI display may be a separate device such as an iPhone, iPad, tablet computer, or other device. If the GUI device is separate from the curing light 10, then preferably the curing light includes a wireless data transfer element (not shown) for communicating with the display for the real-time display of targeting graphics, such as a superimposed bullseye graphic 26 (see FIG. 3). One example of relevant alphanumeric information would be a digital countdown of the remaining cure time. A standard low-cost data transfer solution such as Bluetooth or Wi-Fi is expected. The data transfer solution could be any suitable standard now known or later developed. Further, as an alternative to a wireless data transfer element, the curing light 10 and the separate display device could be connected by a cord. And yet further, the separate GUI device could be omitted if a GUI display (perhaps less abled) could be incorporated into the curing light 10 in a manner considered ergonomically acceptable.

II. Dental Curing Light Operation

The curing light 10 provides coaxial alignment of the curing beam of the light engine 12 and the FOV of the camera 14. The coaxial alignment enables a real-time, straight-on view of the targeted area of the tooth. When the image is displayed on the GUI display (see FIG. 3), a bullseye 26 or similar targeting graphic may be superimposed on the image to identify the actual center of the curing beam for the real-time position of the curing light 10. The bullseye 26 enables the operator to directly and accurately observe the "aim" of the curing beam and to position the curing light 10 to achieve a desired aim. Because the camera is dynamic, the operator may observe the aim during the entire course of the curing exposure time.

The inclusion of the multi-planar dichroic mirror 16 enables the calculation of distance information by way of triangulation, but to do so using the single camera 14. The multi-planar reflective surfaces 32 and 34 on the mirror 16 provide views of multiple regions at multiple angles. As currently constructed, the reflective surface 34 is a relatively narrow or thin "sliver" of reflective material near the center of the FOV provided by the reflective surface 32. The angle of the reflective surface 34 with respect to the reflective surface 32 causes the relatively narrow reflective surface 34 to be in a different plane than the primary reflective surface 32.

Figure 2:
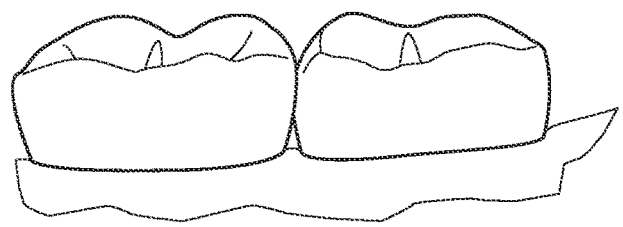
FIG. 2 is a plan image of a tooth including a composite.
Figure 2:
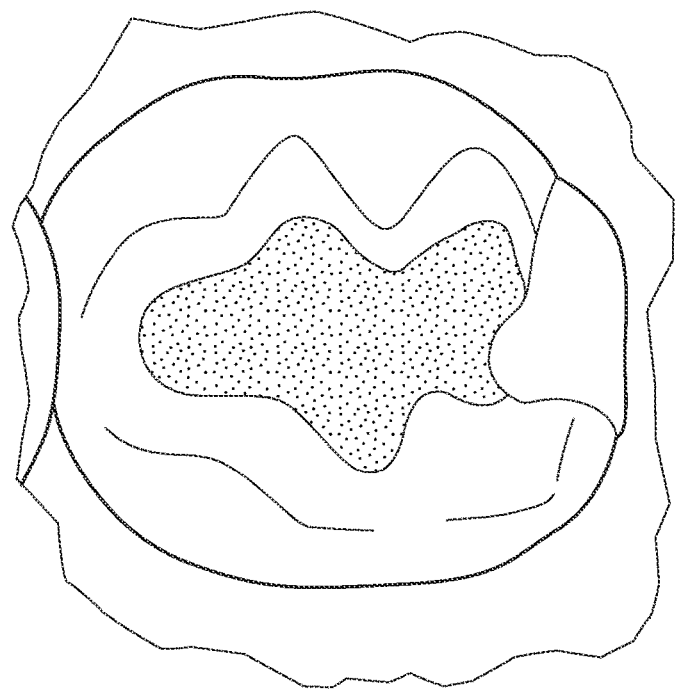

The result is that, as the camera 14 views (a) the majority of the tooth reflected by the primary reflective surface 32 at the primary viewing angle and (b) a relatively narrow band or strip of the tooth reflected by the reflective surface 34 at a secondary viewing angle (different from the primary viewing angle). Consequently, the viewing angles provided by the reflective surfaces 32 and 34 are different. The image received by the camera from the reflective surfaces 32 and 34 is illustrated in FIG. 2. The primary image (reflected from the primary reflective surface 32) is nearly all of FIG. 2, and the secondary image (reflected from the secondary reflective surface 34) is the strip or relatively narrow band 36 which is offset from the remainder of the primary image.

By algorithmically creating a linear "signature" of the pixel string found on either side of the image boundaries 37 and 39 between the two planes, a displacement value between the two signature strings can be determined. The displacement value is representative of the distance between the objective lens 20 and the target.

Therefore, the depth of the composite 30 can be determined by a triangulation process using data derived from the image of a single camera. Further, the irradiance of the beam can be measured and known as a function of the distance of the target from the objective lens for any given light engine power setting. The depth information can be used as an alternate or supplemental means to the measurement of direct reflected intensity measured from the camera data (and preferably averaged over a predetermined array of pixels) to determine the actual irradiance at the targeted surface. This enables a closed loop system providing real-time electrical power control of the light engine so as to achieve a known and controlled irradiance level on the targeted surface.

By storing historical distance information, the system is capable of determining the thickness of the composite 30 that has been placed for any given cure. The thickness information can be further used to control the power applied to the light engine 12.

If the camera 14 includes an auto-focus function, then that function may be used to determine the distance between the lens 20 and the tooth. Determining the distance in this manner may be used as a supplement to the triangulation function described above, or as an alternative to the triangulation function.

The curing light 10 of the present invention provides a number of advantages. The curing light 10 enables the real-time control of the light engine power to maintain a controlled and known amount of irradiance at the intended target independent of operator-induced positional variations. The curing light 10 provides the ability to deliver a known number of joules per $cm^2$ to the target. The curing light 10 provides the ability to view in real time the target area being illuminated by the operator during the cure of the composite, and assists the operator in positional adjustment by way of a bullseye superimposed over the viewed image of the target area. The curing light 10 also provides the ability to measure the thickness of the composite that has been placed for a given cure.

III. Dental Curing Light Control Flow

FIGS. 5-8 illustrate the control flow of the dental curing light 10. The implementation of all of the described steps and functions are well within the capabilities of one skilled in the art. And hence it is unnecessary to describe the steps and functions in greater detail than described herein.

Figure 4:
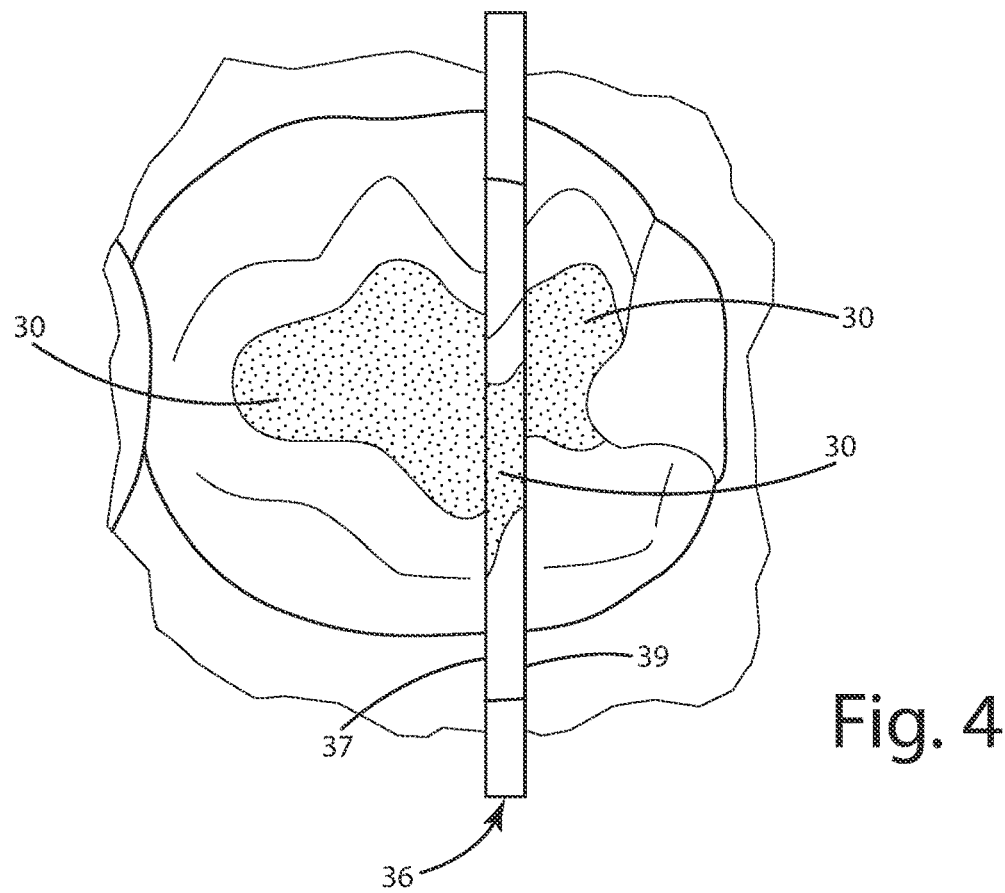
FIG. 4 is a sample camera view of the tooth as reflected by the multi-planar dichroic mirror (MDM).
Figure 8:
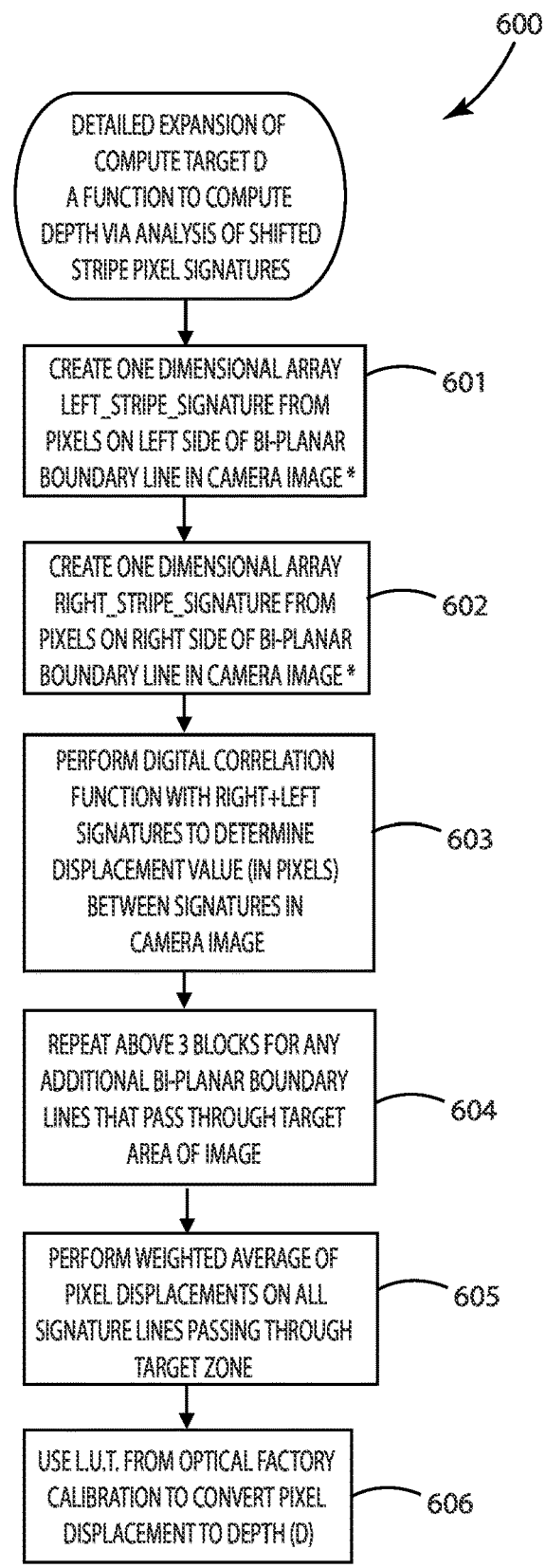

FIG. 8 illustrates the control flow for the Computer Target D function 600. The first step 601 in the function 600 is to create a one-dimensional array Left Stripe Signature from the pixels on the left side of the bi-planar boundary line 37 (see FIG. 4). The second step 602 is to create a one-dimensional array Right Stripe Signature from the pixels on the right side of the bi-planar boundary line 39 (see FIG. 2). The next step 603 is to perform a digital correlation function with the left and right stripe to determine placement values (in pixels) between the signatures in the image.

The steps or blocks 601, 602, and 603 are repeated 604 for any additional bi-planar boundary lines that passed through the target area of the image. The number of such lines will depend in part on the design of the mirror 16 and therefore the number of boundary lines created by the mirror.

As the next step 605, a weighted average of the pixel displacements on all of the signature lines passing through the target zone is calculated. A lookup table (LUT) is then used 606 to convert the pixel displacement to a depth D, which is returned to the calling portion of the program.

Figure 5:
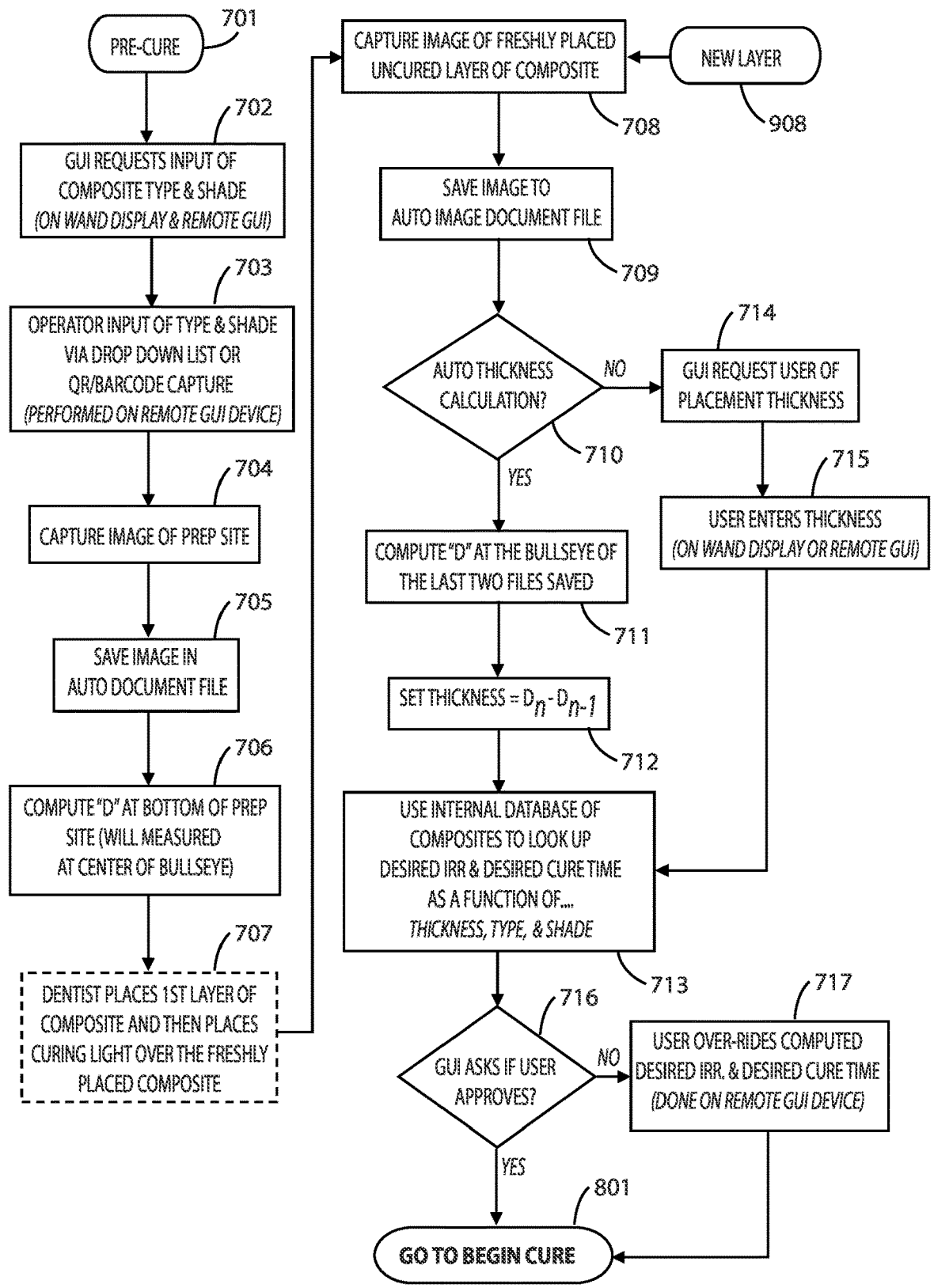
FIGS. 5 through 8 are flowcharts showing the operation of the dental curing light control system.
Figure 6:
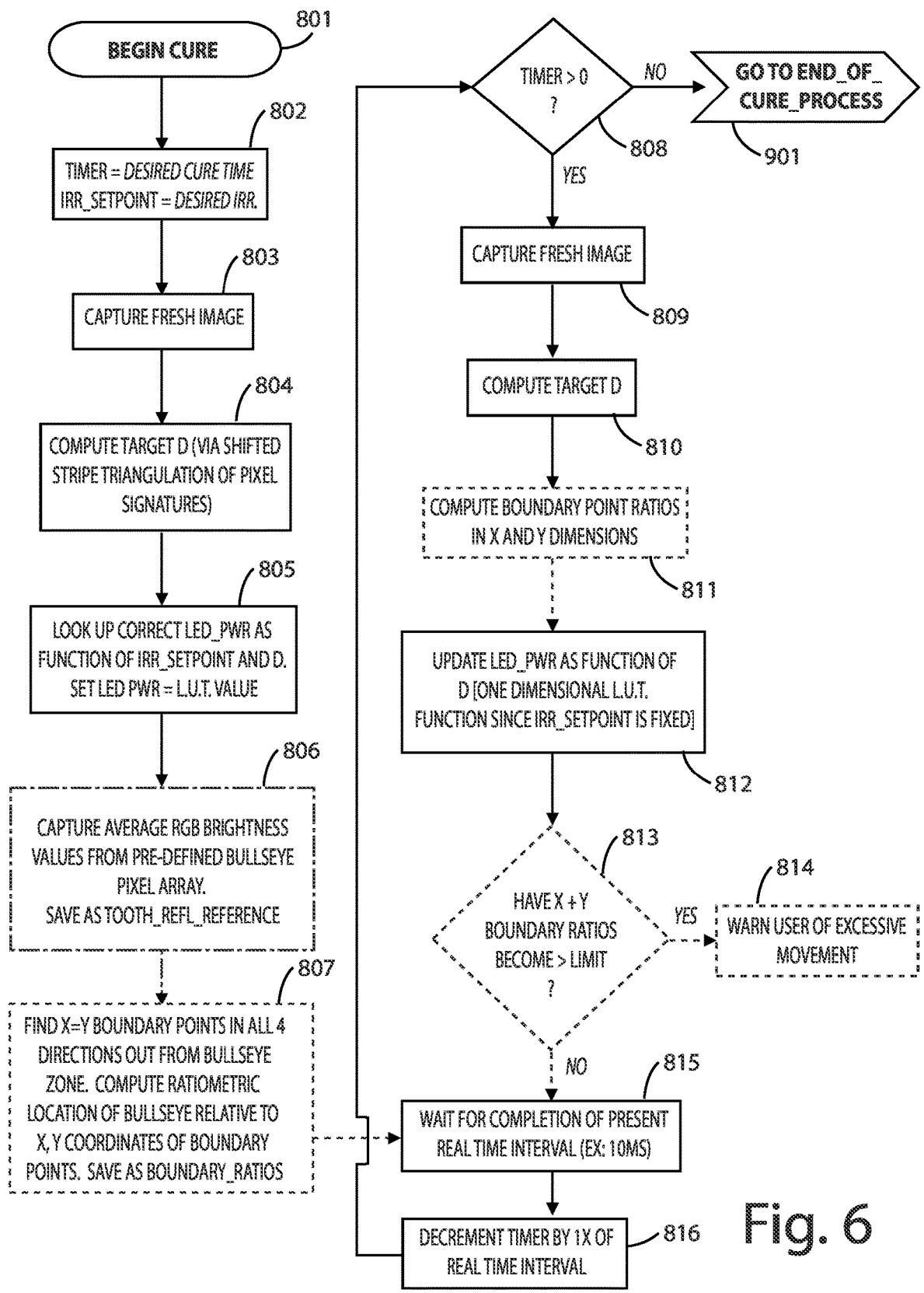
Figure 7:
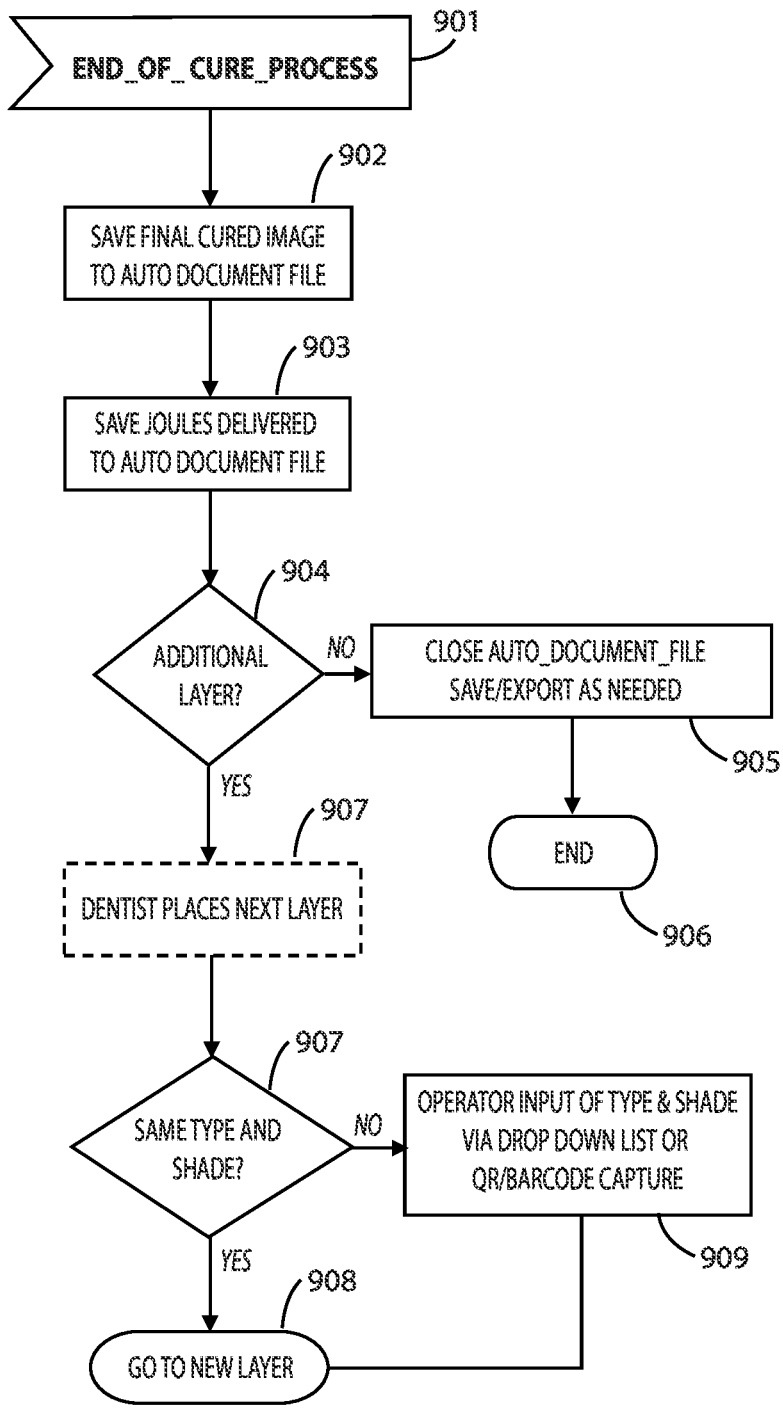

FIG. 5 illustrates the program flow for the "Pre-Cure" function. Program flow starts 701, and the GUI requests 702 input regarding the composite to be used in the restoration. In response, the operator inputs 703 the type, shade, and potentially other information for the composite. The input may facilitated by any suitable technique now known or later developed. Exemplary techniques include drop-down lists, QR/barcode capture, or voice recognition.

The control then captures 704 an image of the prepared site using the output of the camera 14, and the image is saved 705 in an auto document file. The control then calls function Compute Target D 600 (see FIG. 10) to compute 706 the distance to the bottom of the prep site at the center point of the bullseye 26 (see FIG. 6). At this point, the control waits 707 for the dentist to place the first layer of composite within the prepared area and to reposition the curing light 10 over the target area.

The control then captures 708 an image of the target area—now containing a freshly placed layer of composite—and saves 709 the image to the auto document file. The control then determines 710 whether the curing light 10 is operating in auto thickness calculation mode. If the answer is Yes, the control computes 711 D at the bullseye 26 of the last two image files saved. The thickness of the most recently applied composite layer is set 712 as the difference between the depths D of the last two files saved. The control then uses or references 713 an internal database of composite information to look up the desired irradiance and the desired cure time as a function of the type, the shade, and/or the thickness of the composite.

If the control determines that the curing light 10 is not operating in auto thickness calculation mode, the GUI requests 714 the operator to input the thickness of the most recent placement of composite. The users then enters 715 the thickness through the GUI, whether on the bond display or on the separate unit. Program flow then continues with block 713.

Through the GUI, the control then asks 716 if the operator approves the determined irradiance and cure time. If the answer is Yes, control passes to the Begin Cure function 801. If the answer is No, the control permits 717 the operator to override either or both of the determined irradiance and cure time. The operator may enter override information through the GUI.

FIG. 8 illustrates the program flow for the "Begin Cure" function of the control. Program flow starts 801 with the control setting 802 Timer to be the value of the desired cure time and Irradiance Setpoint to be the value of the desired irradiance. A fresh image is captured 803, and the Compute Target D function is called 804 to determine the distance of the light tip 18 from the target. The control looks up 805 the correct LED power as a function of Irradiance Setpoint and D; and the LED power is set to the lookup table (LUT) value.

Using the camera image, the control captures 806 the average brightness values from the predefined bullseye pixel array. The brightness may be in terms of RGB or any other color space. The average brightness is saved as Tooth Reflectance Reference.

In step 807, the control (a) finds the X=Y boundary points (i.e. the transition points between composite and tooth) in all four directions out from the center of the bullseye 26, (b) computes the ratiometric location of the bullseye relative to the X equal Y coordinates of the boundary points, and (c) saves the computed values as the Boundary Ratios. The control then waits 815 for the completion of a predetermined time interval, which in the current embodiment is 10 milliseconds (ms). Following completion of the time interval, Timer is decremented 816 by one time interval. And program flow continues to step 808.

The control then determines 808 if Timer is greater than zero. If the answer is No, then program flow passes to the End of Cure function 901. If the answer is Yes, then the control captures 809 a fresh camera image, and the control computes 810 a new Target D. The control then computes updated Boundary Ratios in the X and Y dimensions. And the control updates 812 the LED power as a function of Target D using the previously noted lookup table.

The control then determines 813 whether the X and Y Boundary Ratios have exceeded a predefined limit. If the answer is Yes, the operator is warned 814 of excessive movement of the curing light 10. The warning may be a visual display on the GUI, an audible sounds, and/or any other suitable technique. If the answer is No, the control passes to step 815.

FIG. 9 illustrates the program flow for the "End of Cure" function of the control. Program flow starts 901 with saving 902 the final image to the auto document file. The control also saves 903 the joules delivered to the auto document file. This could be, for example, a non-dimensional scaler or two-dimensional image map.

The control then queries 904 the operator through the GUI whether an additional layer of composite is to be placed. If the answer is No, control passes to block 905 in which the auto document file is closed, saved, and/or exported as desired. And the function ends 906.

If the answer to the query 904 is Yes, the control waits for the dentist to place 907 the next layer of composite. When the operator indicates that the next layer has been placed, the control asks 907 the operator whether the just-placed layer is of the same type in shade as the previous layer. If the answer is Yes, control passes to the New Layer step 908 (see also FIG. 7). If the answer is No, control passes to step 909, where the operator may input the type and the shade of the just-placed composite as described above before control passes to the New Layer step 908.

Preferably, the control is additionally capable of controlling the spectral content of the light source output to provide a tunable spectrum of light content between approximately 405 nm and 465 nm.

IV. Conclusion

The present invention has been described in conjunction with a dental curing light. It is believed the concepts and techniques described herein may be extended to non-dental applications, such as industrial manufacturing, where precise light cure of adhesives or similar composite fills are required. The curing light 10 compensates for a variety of "positional variables" that can exist between the source generation of the curing light and the intended final target destination of the light. The curing light 10 provides improved compensation for operator variations.

The above descriptions are those of current embodiments of the invention. Various alterations and changes can be made without departing from the spirit and broader aspects of the invention as defined in the appended claims, which are to be interpreted in accordance with the principles of patent law including the doctrine of equivalents.

This disclosure is illustrative and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as alternatives.

Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A method of curing a dental composite within a tooth, the method comprising:
   providing a dental curing light having a light source and a vision system;
   positioning the dental curing light so that the vision system and the light source are aligned with the dental composite within the tooth;
   acquiring an image of the dental composite within the tooth, the image including multiple image portions acquired from different angles using the vision system;
   determining the distance between the light source and the dental composite within the tooth as a function of the multiple acquired image portions;

determining a desired irradiance of the dental composite within the tooth as a function of the determined distance; and controlling the light source as a function of the determined distance to deliver the desired irradiance to the dental composite within the tooth.

2. A method as defined in claim 1 wherein the acquiring step includes using a multi-planar mirror to capture the image.

3. A method as defined in claim 1 further comprising storing information regarding the dental composite, and wherein the controlling step is additionally a function of the stored dental composite information.

4. A method as defined in claim 3 wherein the controlling step includes controlling the spectral content of the desired irradiance.

5. A method as defined in claim 1 wherein the vision system and the light source are coaxially aligned.

6. A method of curing a dental composite within a tooth, the method comprising:

providing a dental curing light having a light source and a vision system;

positioning the dental curing light so that the vision system and the light source are aligned with the dental composite within the tooth;

acquiring an image of the dental composite within the tooth, the image including multiple image portions acquired from different angles using the vision system, the acquiring step including using a multi-planar mirror to capture the image, the multi-planar mirror being dichroic and aligned with the light source beam;

determining the distance between the light source and the dental composite within the tooth as a function of the multiple acquired image portions;

determining a desired irradiance of the dental composite within the tooth as a function of the determined distance; and controlling the light source as a function of the determined distance to deliver the desired irradiance to the dental composite within the tooth.

* * * * *